US012020813B2

(12) United States Patent
Schmidt

(10) Patent No.: US 12,020,813 B2
(45) Date of Patent: Jun. 25, 2024

(54) METHOD FOR SUPPORTING MEDICAL PERSONNEL, SUPPORT SYSTEM, COMPUTER PROGRAM AND DATA CARRIER

(71) Applicant: Siemens Healthcare GmbH, Erlangen (DE)

(72) Inventor: Sebastian Schmidt, Weisendorf (DE)

(73) Assignee: Siemens Healthineers AG, Forchheim (DE)

( * ) Notice: Subject to any disclaimer, the term of this patent is extended or adjusted under 35 U.S.C. 154(b) by 588 days.

(21) Appl. No.: 15/963,395

(22) Filed: Apr. 26, 2018

(65) Prior Publication Data

US 2018/0322953 A1 Nov. 8, 2018

(30) Foreign Application Priority Data

May 2, 2017 (EP) .................................... 17169049

(51) Int. Cl.
*G16H 50/20* (2018.01)
*G16H 10/60* (2018.01)
(Continued)

(52) U.S. Cl.
CPC ............. *G16H 50/20* (2018.01); *G16H 10/60* (2018.01); *G16H 40/63* (2018.01); *G16H 50/70* (2018.01)

(58) Field of Classification Search
CPC ........ G16H 50/20; G16H 10/60; G16H 50/70; G16H 40/63
See application file for complete search history.

(56) References Cited

U.S. PATENT DOCUMENTS 7,593,913 B2 9/2009 Wang
8,238,999 B2 8/2012 Haider
(Continued)

FOREIGN PATENT DOCUMENTS

WO WO 2008031082 A2 3/2008
WO WO-2013/075127 A1 5/2013
WO WO 2016097886 A1 6/2016

OTHER PUBLICATIONS

Kavishwar B Wagholikar et al: "Modeling Paradigms for Medical Diagnostic Decision Support: A Survey and Future Directions"; Journal of Medical Systems; Kluwer Academic Publishers-Plenum Publishers; NE; Bd. 36 Nr. 5; pp. 3029-3049; XP035103437; ISSN: 1573-689X; DOI: 10.1007/S10916-011-9780-4;.
(Continued)

*Primary Examiner* — Eliza A Lam
(74) *Attorney, Agent, or Firm* — Harness, Dickey & Pierce, P.L.C.

(57) ABSTRACT

A method is for supporting medical personnel. The method includes taking account of patient data of the patient in an electronic health record stored in a first database; determining at least one prevalence value, each relating to a diagnosis to be made for a group of people including the patient, to which the patient has been classified as belonging in dependence on at least one part of the patient data; generating, from the at least one prevalence value, at least one item of evaluation information based on at least one future examination procedure performable with respect to the diagnosis to be made, taking into account prediction information present in a second database describing at least one of sensitivity and specificity for the at least one future examination procedure with respect to the diagnosis to be made; and outputting the at least one item of evaluation information to the medical personnel.

28 Claims, 2 Drawing Sheets

| GA1 | 0,001 |
|---|---|
| GA2 | 0,003 |
| ⋮ | ⋮ |

14 → 15

| GA1 | 0,0005 |
|---|---|
| GA2 | 0,321 |
| ⋮ | ⋮ |

17 → 16

| GA1 | 0,0005 |
|---|---|
| GA2 | 0,894 |
| ⋮ | ⋮ |

18, 19

PPV2
NPV2

(51) Int. Cl.
*G16H 40/63* (2018.01)
*G16H 50/70* (2018.01)

(56) References Cited

U.S. PATENT DOCUMENTS

| | | | | |
|---|---|---|---|---|
| 8,321,238 | B2 | 11/2012 | Boehmer-Lasthaus | |
| 8,401,872 | B2 | 3/2013 | Haider | |
| 8,640,053 | B2 | 1/2014 | Hellinger | |
| 2003/0065241 | A1* | 4/2003 | Hohnloser | G16H 10/20 600/1 |
| 2008/0172249 | A1 | 7/2008 | Glaser-Seidnitzer et al. | |
| 2012/0077690 | A1* | 3/2012 | Singbartl | G01N 33/6893 506/9 |
| 2014/0195168 | A1* | 7/2014 | Shaikh | G16H 50/20 702/19 |
| 2015/0100572 | A1 | 4/2015 | Kalafut et al. | |
| 2016/0157807 | A1* | 6/2016 | Anderson | A61B 5/02158 600/427 |
| 2017/0269081 | A1* | 9/2017 | Oved | G01N 33/56983 |
| 2019/0159737 | A1* | 5/2019 | Buckler | G16H 30/40 |

OTHER PUBLICATIONS

Extended European Search Report #17169049.8 dated Jun. 26, 2017.

European Office Action dated Aug. 21, 2019.

European Office Action dated Apr. 28, 2021 for corresponding European Patent Application No. 17169049.8.

* cited by examiner

METHOD FOR SUPPORTING MEDICAL PERSONNEL, SUPPORT SYSTEM, COMPUTER PROGRAM AND DATA CARRIER

PRIORITY STATEMENT

The present application hereby claims priority under 35 U.S.C. § 119 to European patent application number EP17169049.8 filed May 2, 2017, the entire contents of which are hereby incorporated herein by reference.

FIELD

At least one embodiment of the invention generally relates to a method for supporting medical personnel in the examination of a patient by way of at least one examination procedure that in particular includes a measurement, a support system, a computer program and/or an electronically readable data carrier.

BACKGROUND

When patients consult medical personnel, for example physicians, in most cases the medical personnel decide to initiate at least one examination procedure in order to check whether certain health anomalies, in particular diseases, are present or excluded, i.e. in order to be able to make a diagnosis with respect to a specific health anomaly. Such examination procedures, which are frequently also called diagnostic tests, in particular include at least one measurement to be performed on the patient manually and/or at least partially automatically via a suitable examination device, for example imaging, the detection of substances in parts of the anatomy and the like.

U.S. Pat. No. 7,593,913 B2 discloses a system for providing medical decision support for the diagnosis and treatment of disease.

U.S. Pat. No. 8,238,999 B2 discloses a method for displaying at least one medical finding in which at least one part of a body of a patient is shown in a partial body view on a display medium.

U.S. Pat. No. 8,321,238 B2 discloses a method for associating an assessor with an assessment task, in particular an evaluation of an image data set.

U.S. Pat. No. 8,401,872 B2 discloses a method for operating a medical diagnosis apparatus with which medical questions are to be answered.

U.S. Pat. No. 8,640,053 B2 discloses a method for the presentation of multiple image data sets within the scope of a comparative evaluation.

Herein, each diagnostic examination procedure can be assigned a certain sensitivity and specificity, which, as a rule do not equal 100%. Sensitivity indicates the probability of a true-positive patient being identified as positive; specificity describes the proportion of negatively tested people out of all non-positive patients, which means the probability of identifying non-diseased people correctly with a diagnostic test. However, these values are not very significant in practice since it is not actually known whether the health anomaly is present in the patient and whether, therefore, this patient is actually positive (true-positive).

Values that have been suggested as more relevant in practice for the evaluation of examination procedures are the positive predictive value and the negative predictive value (PPV or NPV), wherein the positive predictive value indicates the probability that a positive result also corresponds to a positive correct diagnosis and a negative value indicates the probability that a negative result also corresponds to a negative correct diagnosis. These predictive values can be calculated as follows:

$$PPV=sensitivity*prevalence/(sensitivity*prevalence+(1-sensitivity)*(1-prevalence))$$

$$NPV=specificity*(1-prevalence)/((1-sensitivity)*prevalence+specificity*(1-prevalence))$$

Therefore, prevalence is included in both the PPV and the NPV, wherein, as the prevalence decreases, the PPV decreases as a result of which the value of the examination procedure is reduced and/or it becomes more difficult to justify risks.

Each examination procedure can be assigned a probability function indicating the probability of a true-positive (or true-negative, false-positive or false-negative) diagnosis in dependence on the examination result (test result).

In view of the not absolutely reliable statements, medical diagnoses are generally performed in a multi-stage process with multiple examination procedures. This can be illustrated using the example “lung cancer”. The probability of this for all Germans is approximately 60/100,000 a year. If smoking history is obtained in a first diagnostic step and the person is identified as a heavy smoker, the risk is approximately 30 times greater (1.8/1000). This probability is sufficient to justify an imaging examination, for example computed tomography, despite the associated exposure of the patient to radiation and the costs incurred. If the examination result obtained in such an examination procedure finds a round lesion, the probability increases further; in the case of a small round lesion, for example, to approximately 4/100. Such a probability does not yet justify invasive treatment, only a follow-up examination in a few months. If this follow-up examination identifies a significant growth, the probability increases to approximately ⅔. This probability then also justifies an invasive measure as an examination procedure for diagnosis, for example a biopsy/operation for the final completion of the diagnostic procedure.

Therefore, it can also be stated generally that every medical diagnostic process can be considered to be a sequence of probability conditions in which in each case there is a certain probability that a diagnostic measure, i.e. an examination procedure, will cause a new condition to be entered. Hence, in each step, an initial probability of a possible health anomaly/disease is assumed and the step leads to a resulting probability of this health anomaly being present. Initially, the probability is the general basic value for prevalence in the population, i.e. for this patient or a group of people with the same examination procedures and examination results.

Such considerations have already been suggested in connection with health economics modeling, but they are not applied in clinical practice. Guidelines for medical personnel are not, as a rule, compiled on such a basis and, as a rule, neither do they contain any instructions such as, for example, that a certain examination procedure should only be used in the event of a certain initial probability (prevalence in the group of people to which the patient belongs). The reason for this is that humans find it difficult to ascertain probabilities intuitively and also that probabilities are not known so that an instruction such as “only request diagnostic test when the probability of a positive result is >20%” cannot be implemented in everyday medical practice. To do this, the physician would have already to know for all findings which probability implies which result and this is scarcely practicable. Therefore, nowadays use is generally made of rough classifications, for example the Framingham Risk Score for cardiovascular risk.

Guidelines also follow rough estimations. It is known that some examination procedures only rarely produce a clinically significant positive result, for example in the case of a MRI examination of the spinal columns for sporadic back pain, and hence these are generally advised against. Other examination procedures are recommended in rough dependence on previous findings, but without any precise indication of the PPV from which an examination procedure is justified.

Such problems occur in particular in medical radiology. In many cases, a clear diagnosis based on a radiological examination is not possible, for example in the case of a moderately enlarged lymph node; instead at best it is only possible to estimate a probability. Consequently, radiological findings deliberately contain vague wording ("cannot be excluded") that can be perceived as unsatisfactory by a referring physician. At the same time, it should be noted that human beings are virtually incapable of intuitively comprehending certain probabilities. For example, the probability of an enlarged lymph node being malignant depends on the presence of a primary tumor, but in this case medical personnel are not able to state specific probabilities even though these would be necessary to plan invasive measures.

However, problems of this kind also occur outside the field of radiology. For example, in laboratory diagnostics, relatively arbitrary limit values are defined for laboratory values, even though the probability of a positive diagnosis increases continuously with the laboratory value. It is therefore only reliably possible to specify one probability for each specific laboratory value; any limit value is always defined artificially. Nevertheless, if a limit value is exceeded, it is nowadays frequently assumed that the diagnosis is positive.

Overall, it is established that a diagnostic examination procedure that produces a clear diagnosis is more the exception than the rule. In the majority of cases, only an initial probability of a disease (prevalence) is changed to a (higher or lower) probability for the health anomaly. In present-day medical practice, this is performed purely qualitatively and not quantitatively, thus resulting in a high degree of redundancy and hence additional costs.

SUMMARY

At least one embodiment discloses a possibility for enhanced support of medical personnel that exploits knowledge of the scientifically based informative value of examination results, in particular those obtained by measurement.

Embodiments of the invention provide a method; a support system; a computer program and an electronically readable data carrier. Advantageous embodiments of the invention can be derived from the claims.

At least one embodiment of the present application is directed to a method for supporting medical personnel in the examination of a patient by way of at least one examination procedure, in particular including a measurement. The method includes:

taking account of patient data of the patient in an electronic health record stored in a first database, the patient data including at least one of

- at least one property of the patient and
- at least one examination result from at least one already concluded examination procedure, determining at least one prevalence value, each at least one prevalence value relating to a diagnosis to be made for a group of people including the patient, to which the patient has been classified as belonging in dependence on at least one part of the patient data; and generating, from the at least one prevalence value determined, at least one item of evaluation information based on at least one future examination procedure performable with respect to the diagnosis to be made, taking into account prediction information present in a second database describing at least one of sensitivity and specificity for the at least one future examination procedure with respect to the diagnosis to be made; and outputting the at least one item of evaluation information generated to the medical personnel.

At least one embodiment of the present application is directed to a non-transitory computer readable memory, storing a computer program configured to carry out at least one embodiment of the method when executed on a computing apparatus.

At least one embodiment of the present application is directed to a non-transitory electronically readable data carrier, storing a computer program configured to carry out at least one embodiment of the when executed on a computing apparatus.

BRIEF DESCRIPTION OF THE DRAWINGS

Further advantages and details of the present invention can be derived from the example embodiments described in the following and with reference to the drawings, in which.

DETAILED DESCRIPTION OF THE EXAMPLE EMBODIMENTS

Figure 1:
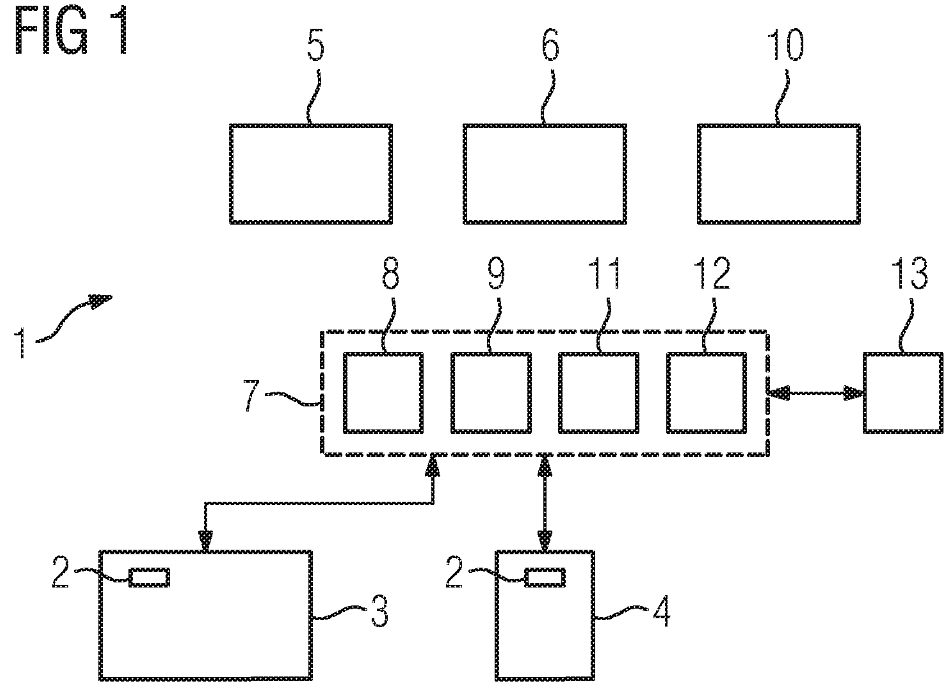
FIG. 1 shows a schematic sketch of an examination system according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as “processing” or “computing” or “calculating” or “determining” of “displaying” or the like, refer to the action and processes of a computer system, or similar electronic computing device/hardware, that manipulates and transforms data represented as physical, electronic quantities within the computer system’s registers and memories into other data similarly represented as physical quantities within the computer system memories or registers or other such information storage, transmission or display devices.

In this application, including the definitions below, the term ‘module’ or the term ‘controller’ may be replaced with the term ‘circuit.’ The term ‘module’ may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

An inventive method of at least one embodiment is for supporting medical personnel in the examination of a patient by way of at least one examination procedure, in particular including a measurement, provides that, taking into account patient data in an electronic health record present in a first database that includes at least one property of the patient and/or at least one examination result from at least one already concluded examination procedure, at least one prevalence value in each case relating to a diagnosis to be made for a group of people including the patient to which the patient has been classified as belonging in dependence on at least one part of the patient data is determined and from the prevalence value at least one item of evaluation information based on a future examination procedure that can be performed with respect to the diagnosis to be made is generated taking into account prediction information present in a second database describing the sensitivity and/or the specificity for the at least one future examination procedure with respect to the diagnosis to be made and output to the medical personnel.

Therefore, according to at least one embodiment of the invention, it was identified that an evaluation of the highly complex physico-technical relationships within the context of the examination procedures/diagnostic tests that humans find it difficult to ascertain intuitively is enabled for the first time by way of a suitable computing system. Results achieved by an extremely diverse range of measurements, i.e. basic physico-technical aspects in the diagnostic procedure, which is ultimately a measuring procedure, are combined by technical devices in order to provide added value in respect of the further course of the overall diagnostic process for medical personnel. Herein, use is made in particular of a context, which is anyway further developed during the technical implementation, namely the so-called electronic health record, in which patient data relating both to properties of the patient, in particular with respect to medical history and examination procedures performed and to the results thereof can be stored as patient data.

First, a prevalence value based on the patient data defining the group of people to which the patient belongs is determined, i.e. a patient-related probability that a certain health anomaly, in particular a disease, is present, wherein there are two basic options for the determination, as will be explained in more detail below. Herein, it is also preferable for prevalence values for different diagnoses to be made, i.e. different health anomalies, always to be kept up-to-date in the health record so that, after determination, the prevalence value ultimately becomes part of the patient data where it is in principle available when support is required for new examination procedures. Obviously, herein the prevalence value should always be kept up-to-date, which means, new examination procedures and examination results, which, as explained in the introduction, shift the probabilities, are to be taken into account.

The first and the second database can be combined, in particular be present on the same computing apparatus and/or in the same cloud; however, it also conceivable for the first database and/or the second database to be partitioned, for example as a distributed system and/or implemented with a cloud on different computing apparatuses and/or even, for example, for the electronic health records always to be stored in the medical apparatuses where the patient is at present in treatment.

As already explained, the diagnosis to be made in particular relates to a specific health anomaly or health problem, in particular a disease, i.e. it has the object of identifying the presence or absence of the health anomaly as reliably as possible. Accordingly, it is also expedient for, as noted, up-to-date prevalence values for the patient to be stored in the electronic health records since then already-determined prevalence values are available for different diagnoses to be made, for example in the context of check-ups for different typical diseases. Herein, it should be noted, that even it is performed in respect of one specific health anomaly, an examination procedure can definitely have an influence on multiple prevalence values.

To summarize: it is therefore possible for a plurality of different evaluation results combining knowledge of the prevalence of diseases and the measuring techniques for examination procedures to be analyzed in one support system in order to support medical personnel in examination procedures that are still to be performed such that an optimum examination of the patient, preferably in numerous aspects, is enabled. Concepts of the physico-technical relationships that are difficult for humans to ascertain intuitively are analyzed automatically and in the background, in particular with respect to concatenated probabilities and/or modeling of patient conditions with respect to health anomalies to be diagnosed in order to provide evaluation information useful to humans and to improve the treatment of the patient, in particular with respect to a diagnosis that is as reliable as possible and/or optimum utilization of the technical possibilities.

In one expedient embodiment, prediction information can be used in the form of a sensitivity value and a specificity value and/or a ROC curve. Herein, it is preferable for the probability functions used to be so-called ROC curves for the examination procedures/diagnostic tests, which may, for example, be known from studies. ROC curves (receiver-operating-characteristic curves), often also called threshold-value optimizing curves, are a method for the evaluation and optimization of analytic strategies. Herein, it is, for example, possible for resulting relative frequency distributions for possible parameter values for both input data and examination results to be given in the form of sensitivity (true-positive rate) and specificity. Hence, the prediction information in particular provides an excellent basis, in order, for example, to determine predictive values, i.e. in particular the positive predictive value (PPV) and the negative predictive value (NPV).

There are essentially two possible approaches for determining the prevalence value; these can also be combined.

For example, it can on the one hand be provided that the prevalence value is at least partially determined on the basis of a basic value for a group of people defined by patient properties taking into account available examination results and the prediction information assigned to the already concluded examination procedure. Therefore, this enables retrospective modeling of the patient. The starting point is a basic value for a group of people in the population to which the patient belongs and which can be determined with reference to patient properties. Herein, patient properties can describe multiple items of information, for example the patient's gender, information on the patient's build (for example body mass index), the patient's habits (smoking etc.), the age of the patient and/or classification into risk groups. Therefore, patient properties can also include results from the medical history.

Now, prevalence values specifying the general probability of the presence of a health anomaly are available or determinable for the respective groups of people, for example using a third database. Proceeding from this basic value, the probability is modified by examination results from already-performed examination procedures relating to the diagnosis to be made. Since it is known from the prediction information how the probabilities shift, it is therefore, possible, in particular using probability models describing the probability chains, to determine a current probability of the patient having the health anomaly and hence a current prevalence value.

However, it is furthermore particularly advantageously possible within the context of the present invention to utilize the multiple items of data and examination results provided by the multiple electronic health records for different patients in order to determine prevalence values in this way. For example, it can be provided that the basic value and/or the prevalence value for the respective group of people is determined at least partially in dependence on patient data for further patients belonging to the respective group of people acquired in the first database for which a ground truth with respect to the diagnosis to be made is known or derivable. It is only at the latest on the death of a patient and/or a highly reliable diagnosis that it is known whether the health anomaly is or was actually present in the patient so that a ground truth exists.

Since it is difficult to prove the absence of a health anomaly reliably, it is possible for corresponding, in particular temporal, conditions to be created under which it can be assumed that a health anomaly is not present in a patient and this can also be understood to be a ground truth. For example it can be provided that, for further patients, for whom an examination procedure relating to the diagnosis to be made has already been performed that does not provide a ground truth, in the event of no further examination occurring within a predefined time interval and/or no evidence being obtained in the time interval of the presence of the specific health anomaly to which the diagnosis to be made relates, it is assumed that a negative diagnosis is a ground truth. If, for example, a certain diagnostic test was performed two years ago as an examination procedure but the patient has not so far been examined further or identified as positive, it can be assumed that the patient is not diseased. It is also possible to assume a negative diagnosis as a ground truth for patients who have never been suspected of having the health anomaly.

Such ground truths, which can be determined from the first database, can, together with the patient data, now be used with groups of people that have been identified sufficiently accurately by the electronic health records to determine prevalence values for correspondingly matching patients in the patient data from the first database and hence the actual health records. Therefore, in this way there is a further evaluation of physical issues that are used in a beneficial way to determine evaluation information for medical personnel.

Herein, however, it is stressed that such ground truths can obviously also be derived from the first database for determining prediction information. For example, it can be provided that the prediction information for an examination procedure is determined at least partially in dependence on patient data for further patients acquired in the first database subjected to the examination procedure for which a ground truth with respect to the diagnosis to be made is known or derivable. Therefore, if for example, for certain examination procedures, the prediction information, in particular probability information, is not already known from scientific studies or in some other way, if a large number of electronic health records is available, it is possible for the corresponding prediction information to be determined by way of the first database.

Whenever definitive diagnoses, i.e. ground truths, are available for patients, it is simple retrospectively to calculate, for example, probability functions and/or other items of prediction information for diagnostic tests to which as yet no prediction information is assigned in the second database. Therefore, information on the informative value of physical examination results is advantageously derived from a plurality of available data items in order to provide prediction information that can be used to determine prevalence values and/or evaluation information.

Numerous specific functions can be implemented for a support system of the kind described. Herein, it is noted again at this point that, exactly like the evaluation information, the prevalence value does not represent an actual diagnosis or the like, but only a calculated value describing statistical and optionally physico-technical relationships. The diagnosis still to be made remains exclusively at the discretion of the medical personnel, in particular the physician, on the basis of the appraisal of different examination results and corresponding conclusions. The evaluation information only provides an indication of the ways in which to arrive at the information required to make the actual diagnosis with the greatest possible degree of reliability or efficiency.

There are numerous possibilities for the specific support of medical personnel. For example, it can, for example be provided that an item of evaluation information for at least one future examination procedure is automatically generated when a prevalence value exceeds a specific threshold value in particular for the diagnosis to be made. Frequently, threshold values exist from which an examination procedure can be considered to be desirable and/or the reimbursement of costs or the like is enabled. Such threshold values can be used in order, when retrieving the electronic health record of a patient for example, to automatically suggest the corresponding examination procedure when the threshold values are exceeded.

If, for example, the prevalence value is greater than a percentage or if, taking into account the current prevalence value, a positive predictive value (PPV) greater than a certain percentage is obtained, the corresponding diagnostic test can be suggested and the examination result taken into account once again in order to determine updated prevalence values and the like until it is possible to flag the diagnosis as confirmed, in particular by the medical personnel. A recommendation for an examination procedure can then also be made if a new item of patient data is determined and/or input. For example, a significant increase in the prevalence value for lung cancer can be expected if there is a history of smoking. If the patient is also of advanced age, a corresponding threshold value for the recommendation of certain examination procedures may be exceeded. Corresponding examination procedures can then be recommended as evaluation information.

The evaluation information can in particular be determined for a user-selected examination procedure. For example, with an up-to-date prevalence value and knowledge of the prediction information, in particular relating to sensitivity and/or specificity, using the formulas named in the introduction, it is easily possible to determine accurate predictive values, in particular PPV and NPV, for the patient or the corresponding group of people to which the patient belongs. This is, for example, expedient when an examination procedure to be performed has been selected by medical personnel when the electronic health record has been opened.

For example, this may produce an output of the type "With a positive test result, there is an 83% probability that the patient is actually diseased, with a negative result there is an 87% probability that the patient is actually healthy—do you want to carry out the test?". In particular, in this way medical personnel can cause predictive values to be displayed for different possible examination procedures and, for example, with respect to whether an exclusion or confirmation is to be made, assess whether the examination procedure should actually be performed.

As already indicated, the evaluation information determined can preferably include at least one recommended examination procedure, in particular a series of recommended examination procedures. However, the supporting method according to the invention has been found to be particularly advantageous precisely in respect of a complete further examination strategy, i.e. a series of further examination procedures. Herein, it can be specifically provided that a series of examination procedures in an optimization method including at least one examination procedure is determined as evaluation information, wherein the optimization is performed with respect to the reliability of a positive diagnosis and/or the reliability of a negative diagnosis and/or the cost-effectiveness and/or the time required for the examination procedures and/or at least one boundary condition targeted at minimum reliability is used. Therefore, this enables the series of further examination procedures that is most favorable and suitable with regard to different aspects with respect to the diagnosis to be made to be determined.

For example, it is possible to identify the most cost effective and/or quickest further procedure that nevertheless (as a boundary condition) provides sufficient reliability for the final overall diagnosis, for example a minimum PPV or NPV specified after the last examination procedure. Such functions can, for example, be selected on a targeted basis by a user, for example by using a user interface providing access to the support system according to the invention. Herein, it is preferably possible to use simulations and/or mathematical probability models, for example a simulation of the development of PPV and NPV via different paths, i.e. different sequences of different procedures. Herein, this can particularly advantageously also include health-economic parameters, for example costs of the diagnostic tests.

Overall, as already explained, it is particularly preferable for the future (or already-performed) examination procedure to be calculated and/or simulated in a mathematical probability model for the determination of the evaluation information (and optionally for the determination of the prevalence value using prediction information). Herein, it is particularly advantageous to use a Bayesian network and/or a Markov chain as the probability model and/or for the simulation to include a Monte Carlo simulation. Therefore, it is possible to use suitable mathematical methods for modeling the chain of diagnostic tests, which are in particular also used in statistics, in particular Bayesian networks and/or Markov chains. Herein, simulation can in particular be performed with respect to the development of PPV and NPV over multiple examination procedures, for example using a Monte Carlo simulation.

A further function available with at least one embodiment of the invention provides that the evaluation information includes a list of examination procedures for which the prevalence value exceeds a limit value describing their reliability. Therefore, in particular when specifications exist that have to be fulfilled to enable certain examination procedures to be used, one expedient functionality can be to list reliable further diagnostic tests.

A further advantageous embodiment of the present invention provides that, during the determination of the evaluation information, at least one item of availability information with respect to the at least one future examination procedure, in particular retrieved from an information system, is taken into account. Herein, it is expedient for the support system according to the invention to be, at least partially, integrated in an information system, for example a hospital information system and/or a radiology information system. In each case, it can expediently be provided that an exchange with such an information system is performed in order also to check the availability of examination procedures and take them into account accordingly during the determination of the evaluation information.

For example, an examination procedure may be temporarily unavailable if a corresponding examination device is overloaded; long-term unavailability is also conceivable if a medical apparatus on which the support method is being performed does not have the necessary examination device and the like. Therefore, a coupling between an information system and a support system according to the invention enables a more in-depth assessment of possible future examination procedures specific to the situation of the medical personnel.

In a development of the method according to at least one embodiment of the invention, it can also be provided that, in a future examination procedure to be performed via medical examination technology, an examination protocol matched to the group of people is determined as evaluation information and sent to the examination device and/or implemented there and/or the evaluation information is at least displayed on the examination device. Since the diagnostic question is already known in the support system, it is therefore also possible for suitable examination protocols for the best possible examination results to be already selected by the support system and in particular also to be provided to the examination device, for example imaging protocols.

In a preferred embodiment, these examination protocols can be further adapted in dependence on the patient data, for example optimized for the patient. This further simplifies the work of the medical personnel and also supports them in respect of the maximum possible automation of the performance of the future examination procedure. In particular, it is also possible in the context of the present invention to submit enquiries to the support system on an actual examination device and obtain a corresponding display of evaluation information.

For example, the examination device can provide software, which is embodied for communication with further components of the support system and forwards corresponding enquiries and receives the evaluation information. The concept of the distributed support system, in particular using so-called "apps" can obviously also be extended, for example to mobile devices carried by medical personnel and the like. If is furthermore also conceivable to provide access to the support system via an access portal, in particular via the Internet.

In addition to the method according to at least one embodiment of the invention, at least one embodiment of the invention also relates to a support system i.e. in particular comprising:

- a first database with electronic health records for a plurality of patients, which in each case contain patient data with at least one property of the patient and/or at least one examination result from at least one already concluded examination procedure on the patient,
- a second database with prediction information describing the sensitivity and/or the specificity in each case for an examination procedure with respect to a diagnosis to be made in each case,
- a classification unit for assigning a patient to a group of people in dependence on at least one part of the patient data for the patient and a diagnosis to be made,
- a prevalence-determining unit for determining a prevalence value relative to the diagnosis to be made for the patient in dependence on the group of people and/or the patient data,
- an evaluation-information-determining unit for determining evaluation information based on at least one future examination procedure that can be performed with respect to the diagnosis to be made taking into account the prevalence value for the diagnosis to be made and the patient and the prediction information for the at least one examination procedure, and
- an output unit for the evaluation information.

All statements with respect to the method according to the invention also apply correspondingly to the support system according to the invention. In particular, as explained, the prevalence-determining unit can determine prevalence values in alternation or in combination on the basis of a basic value for a baseline group of people or evaluate the content of the first database correspondingly. Therefore, the classification unit can, for example on the basis of patient properties, assign the patient to a group of people, for which a basic value for the prevalence is available, for example in a third database, wherein then the prevalence-determining unit can derive an up-to-date prevalence value herefrom using already-performed examination procedures if the prediction information for the already-performed examination procedures is available. Obviously, such a third database can also be used to store prevalence values for groups of people, who have been classified using examination results for performed examination procedures; finally, as already explained with respect to the method, such prevalence values can also be derived from patient data in the first database.

A support system according to at least one embodiment of the invention can also include further units and subunits and can in particular, be implemented, at least partially, in a cloud and/or as part of a cloud. Coupling to external information systems is also possible. Further functional units of the support system according to the invention can, for example, be evaluation units for determining basic values and/or prevalence values and/or prediction information based on the patient data. Furthermore, the support system can also include software, which can, for example, be provided on mobile devices and/or examination devices in order to provide a user interface to the support system.

For example, a computer program according to at least one embodiment of the invention can be loaded directly into a memory of a computing apparatus and comprises program segments to carry out the steps of at least one embodiment of the method described herein when the computer program is executed in the computing apparatus. The computer program can be stored on an electronically readable data carrier according to the invention, which therefore includes electronically readable control information stored thereupon, which includes at least one such computer program and is embodied to carry out a method described herein when the data carrier is used in a computing apparatus. The data carrier is preferably a non-transient data carrier, for example a CD-ROM.

FIG. 1 is a schematic sketch of a support system 1 according to the invention. In the present case, the support system 1 is implemented by at least one computing apparatus, typically multiple computing apparatuses, which in turn can represent a cloud, at least partially. The support system 1 can communicate via suitable interface 2, for example so-called "apps" as software and/or Internet portals, with examination devices 3 for performing an examination procedure, mobile devices 4, which can, for example, be assigned to medical personnel, and further external and/or only partially used computing apparatuses.

The support system 1 comprises a first database 5 in which patient data for different patients is stored in the form of electronic health records. Herein, the patient data includes both properties of the patient and already-performed examination procedures and the examination results thereof. Furthermore, also stored as part of the patient data are prevalence values for different diagnoses to be made, i.e. different specific health anomalies, in particular diseases, in the electronic health records, the determination and updating of which will be discussed in more detail below.

For the determination of prevalence values for patients, the at least one computing apparatus 7 of the support system 1 comprises a classification unit 8 and a prevalence-determining unit 9. The classification unit 8 can be used to evaluate the patient data in first database 5 in order to assign the patient to at least one group of people, which is taken into account on the determination or updating of prevalence values via the prevalence-determining unit 9. In this case, there are two conceivable basic possibilities, that can also be used cumulatively, for the determination of prevalence values for certain diagnoses to be made for a patient via the prevalence-determining unit 9. It is possible, on the one hand, for the groups of people also to take account of already-performed examination procedures and examination results thereof, wherein it is also possible to assign the prevalence values directly to the corresponding groups of people taking into account the performed examination procedures, which can, for example, be retrieved from an optional third database 10 and/or derived from patient data in the first database 5, wherein there is already a ground truth with respect to the diagnosis to be made for these patients, i.e. the patient data for these further patients contains a diagnosis considered to be confirmed, which can, for example, be based on a final evaluation by medical personnel or from which it may also be concluded that, for a certain interval, for example from a certain examination procedure, there are no further entries with respect to the health anomaly, so that it may be assumed that the health anomaly is not present in the patient. As the number of patients acquired in the first database 5 increases, the accuracy of such a determination of a prevalence value increases.

However, it is also conceivable to proceed from a basic value for a group of people to which the patient belongs, in particular once again stored in the optional database 10, and to model the development of the prevalence on the basis of already-performed examination procedures and the sensitivity/specificity thereof, in particular using a probability model. Herein, if sufficient ground truths are available with respect to further patients, it is obviously also possible to derive the basic values mentioned from the patient data in the first database 5.

Prediction information relating to different examination procedures and describing the sensitivity and specificity thereof are stored in a second database 6 of the support system 1. The prediction information enables the modeling, wherein said modeling preferably contains ROC curves. The prediction information can be known from studies and/or other scientific measurements and stored in the second database 6; however, it is also possible, to determine prediction information for examination procedures using the patient data in the first database 5 and the already-discussed ground truths. Once determined, up-to-date prevalence values are also stored as patient data in the corresponding electronic health records and can be displayed if required, but are in principle used for determining evaluation information, as will be explained in the following. Herein, the prevalence values stored in the first database 5 can be continuously kept up-to-date, for example updated, as soon as information on a new patient property, for example smoking history, becomes available, a new examination procedure has been performed and input and/or another trigger event occurs, for example the patient is assigned to a new age group on the basis of their date of birth.

Then, an evaluation-information-determining unit 11 determines an item of evaluation information for at least one future examination procedure to be performed with respect to the diagnosis to be made. Herein, both the prevalence values and the prediction information for the at least one examination procedure from the second database 6 are taken into account. Depending upon which functionality of the support system 1 is desired at present, different ways are conceivable for determining the evaluation information or selecting the content thereof, which are dealt with in more detail with regard to the method with reference to FIG. 2. Furthermore, the support system 1 includes an output unit 12, which can also be implemented at least partially by interface 2 and is used to output the evaluation information determined to medical personnel. To this end, it is possible to activate suitable display devices, for example displays and/or monitors, accordingly.

Finally, it should already be noted that, when determining evaluation information, it is also possible to take account of external information, for example from an information system 13 that communicates with the support system 1. The information system 13 can, for example, be a hospital information system and/or a radiology information system.

Figure 2:
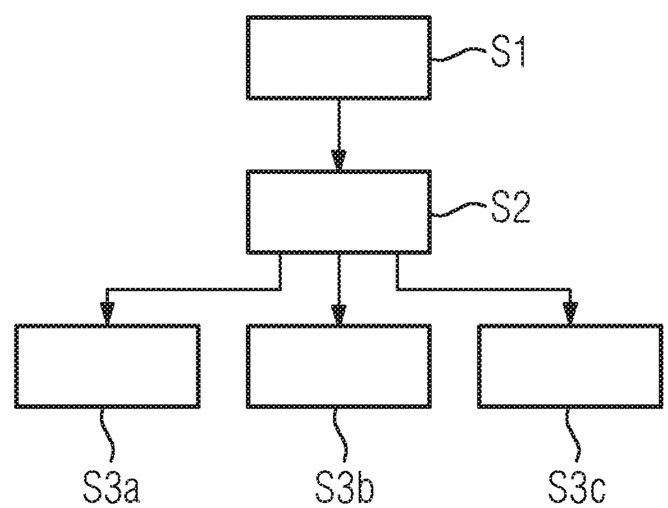
FIG. 2 shows a flow diagram of an example embodiment of the method according to an embodiment of the invention.

FIG. 2 explains the functionalities provided by the support system 1 in more detail with reference to an example embodiment of the method according to the invention. Herein, in a Step S1, as already described, the patient is classified as belonging to a group of people and, in a Step S2, again as already described, prevalence values are determined.

User inputs and/or trigger events can now be used to activate different support functions of the support system 1 of which three are depicted by way of example by Steps S3*a*, S3*b* and S3*c*.

According to Step S3*a*, a continuous check is performed as to whether, on a new determination/updating, an up-to-date prevalence value exceeds a specific threshold value for a diagnosis to be made from which at least one specific examination procedure/diagnostic test is displayed. If the corresponding threshold value is exceeded, the performance of the corresponding examination procedure is automatically recommended, in particular supplemented by further information on the future examination procedure, for example predictive values.

Step S3*b* relates to a user-triggered list of permissible examination procedures. If examination procedures can only be performed with certain criteria, which evaluate prevalence values, these functions may be used to display a list of possible, i.e. permissible, examination procedures, which satisfy the criteria.

One particularly advantageous function is described by Step S3*c* in which modeling and simulation is used to determine an optimum further diagnostic process, i.e. a sequence of examination procedures to be performed. The development of the prevalence values or predictive values, here the PPV and the NPV, is simulated in a Monte-Carlo simulation on a probability model, wherein the modeling can be based on Markov chains and/or Bayesian networks. Herein, the optimization can relate to the greatest possible reliability of the diagnosis, either with respect to the positive diagnosis (maximum PPV) or the negative diagnosis (maximum NPV) or also take account of health-economic factors in the optimization or focus thereupon, if sufficiently reliable diagnoses are verified by way of boundary conditions. Health-economic viewpoints can relate to the speed of performance of the examination procedures and/or the costs of performance of the examination procedures. In the case of optimization with respect to a plurality of optimization targets, in particular a target function, it is possible to use suitable weighting factors, which can in particular also be set by the user.

Figure 3:
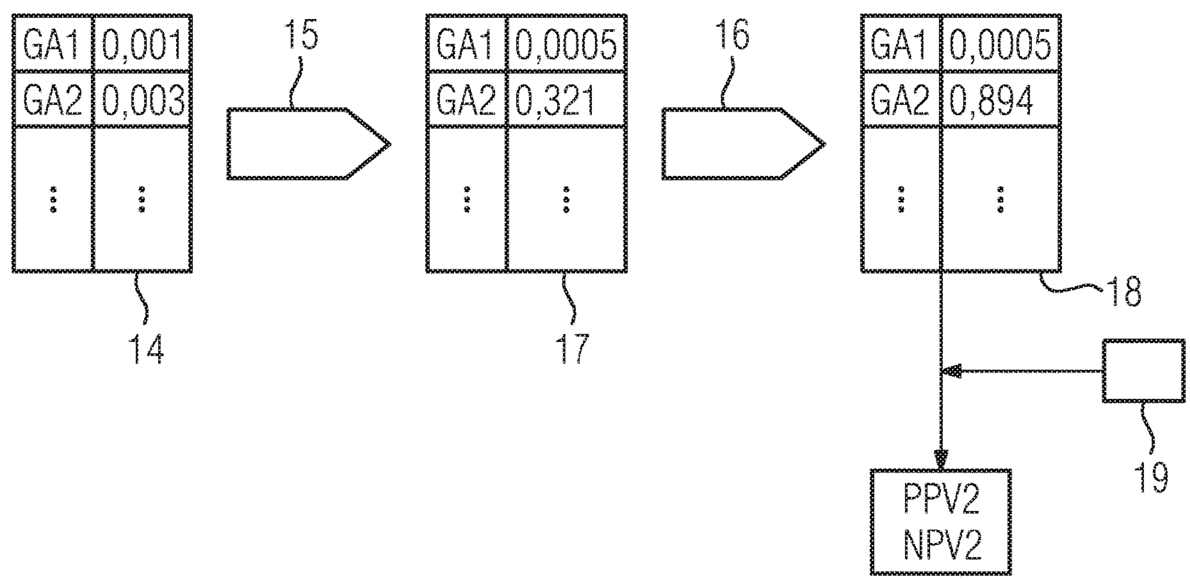
FIG. 3 shows a drawing for modeling probability developments by examination procedures.

FIG. 3 illustrates the evolution of prevalence values used in the context of the present invention based on examination procedures and the prediction of the impact of further examination procedures. In a first probability condition 14, prevalence values exist for multiple health anomalies GA1, GA2, etc., which here still represent basic values solely based on the patient properties, which can already include a medical history, since no examination procedures have been performed with respect to the diagnosis to be made, which can, for example, relate to the health anomaly GA2. The arrow 15 now symbolizes the performance of examination procedures relating to the diagnosis to be made, i.e. diagnostic tests, and the corresponding supplementation of the patient data. In the probability condition 17, the probabilities have evidently already changed, wherein it should be noted that examination results for an examination procedure with respect to a diagnosis to be made can also influence other health anomalies and the prevalences thereof if the diagnosis to be made does not also relate more than one health anomaly (differential diagnosis). The probability of the presence of the health anomaly GA2 has evidently already increased.

According to a further examination procedure, arrow 16, there is a third probability condition 18 with which the probability of the presence of the health anomaly 2 has already significantly increased. Nevertheless, it is now, for example, necessary to consider which at least one further examination procedure should be performed in order to be able to confirm the diagnosis. To this end, in the example shown in FIG. 3, the prediction information 19 in the second database 6 is used to determine predictive values, i.e. PPV and NPV, for the diagnosis to be made for different possible examination procedures and to select the optimum examination procedure to be performed, for example the one that is likely to provide the best PPV or NPV for the health anomaly 2.

This will be explained in more detail with reference to a few examples. From computed tomography data, it is possible to use flow simulation to determine the FFR (fractional flow reserve), which is defined as the quotient of the pressure after a stenosis and the pressure before the stenosis. Herein normally a value of less than 0.75 is considered to be pathological. For this examination procedure, a sensitivity of approximately 90% produces a specificity of approximately 70%. A basic value for a prevalence of 1% (general population) produces a positive predictive value for the tests of 2.9%, which means 2.9% of those with positive test results are actually diseased. This is too low to justify an invasive measure. Therefore, the support system could, for example, output the following as evaluation information: "Probability of disease 2.9%, invasive measures not justified". However, a lower test value, for example 0.5, meaning a higher specificity, for example 99%, at the expense of sensitivity, would produce an PPV that justifies further diagnostic tests, in particular also invasive examination procedures (48%). In such a case, the prediction information would contain ROC curves assigning the examination result (FFR) to sensitivities and specificities. Therefore, for the patient in the example, with an examination result of 0.5, the evaluation information would justify an invasive measure for further examination.

If, in the cited example, further preliminary examinations are taken into account, for example a higher calcium value, as a result of which is clear that the prevalence value for this patient is significantly higher, for example 30%, even a FFR of 0.75 would produce a PPV of 56%, which would justify invasive measures.

As explained, the support system 1 also enables the derivation of the further diagnostic tests, i.e. examination procedures which would produce the maximum PPV for the lowest expenditure, wherein, in the cited example, it is simple to request further levels of risk as patient data (age, weight, cholesterol level, blood pressure) in order to assign the patient to the correct group of people and determine the prevalence value more accurately so that the expected PPV is increased to an appropriate value or reduced to a value that renders further examination procedures unnecessary. Reference is made to the fact that the above example is obviously simplified since, in reality, the support system would include not only the FFR and the calcium score, but all patient data relating to the diagnosis to be made contained in the electronic health record.

In a further example, a recommendation as evaluation information with respect to a lymph node could, for example, be worded as follow: "A biopsy should be performed for this lymph node as this is appropriate. A positive result would have a predictive value 98%, a negative result would have a predictive value of 56%." It should be noted that it is obviously also possible also to output prevalence values, in particular on request, although these do not themselves represent a diagnosis.

Although the invention was illustrated and described in more detail by the preferred example embodiment, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for supporting medical personnel in examination of a patient using a future examination procedure, the method comprising:

determining, by processing circuitry, a patient prevalence value relating to a diagnosis for the patient based on a group prevalence value for a group of people, a first examination result and previous examination prediction information associated with a previous examination procedure, the patient being classified in the group of people based on first patient data, the first patient data including the first examination result from the previous examination procedure, and the first examination result including a calcium value;

automatically generating, by the processing circuitry, evaluation information related to the future examination procedure based on the patient prevalence value and future examination prediction information in response to determining that the patient prevalence value exceeds a threshold for the diagnosis, the future examination prediction information including a sensitivity and a specificity of the future examination procedure with respect to the diagnosis, and the evaluation information including an imaging protocol optimized for the patient according to the first patient data;

sending, by the processing circuitry, the evaluation information to an imaging device to perform the future examination procedure based on the evaluation information; and performing, by a processor of the imaging device, a computed tomography examination included in the future examination procedure in response to receiving the evaluation information, the performing the computed tomography examination including implementing the imaging protocol, the performing the computed tomography examination including directing a radiation dose to the patient.

2. The method of claim 1, wherein the previous examination prediction information includes at least one of:

a sensitivity value and a specificity value; or a ROC curve.

3. The method of claim 1, further comprising:

determining at least one of the patient prevalence value or the group prevalence value based on second patient data, the second patient data corresponding to (i) a plurality of other patients in the group of people or (ii) a plurality of other patients previously subjected to a particular examination procedure for which a ground truth for the diagnosis is derivable; and determining the previous examination prediction information corresponding to the previous examination procedure based on the second patient data.

4. The method of claim 1, wherein the evaluation information includes at least one of:

a positive predictive value; or a negative predictive value.

5. The method of claim 1, wherein the evaluation information includes at least one recommended examination procedure.

6. The method of claim 5, wherein the evaluation information includes a series of examination procedures; and the method further comprises determining the series of examination procedures based on a boundary condition associated with reliability and at least one of:

a reliability of a positive diagnosis, a reliability of a negative diagnosis, cost-effectiveness, or a duration associated with examination procedures among the series of examination procedures.

7. The method of claim 1, further comprising:

performing a calculation or a simulation corresponding to the future examination procedure using a mathematical probability model, wherein the automatically generating evaluation information generates the evaluation information based on a result of the calculation or the simulation.

8. The method of claim 1, wherein the evaluation information includes a list of examination procedures for which the patient prevalence value exceeds a limit value associated with reliability.

9. The method of claim 1, wherein the automatically generating evaluation information generates the evaluation information based on availability information associated with the future examination procedure.

10. The method of claim 1, further comprising:

causing the imaging protocol to be displayed on the imaging device.

11. A support system, comprising:

a first database storing patient data for a plurality of patients, the patient data including a first examination result from a previous examination procedure on one of the plurality of patients, the first examination result being a calcium value;

a second database storing future examination prediction information including a sensitivity and a specificity for each of at least one future examination procedure with respect to a corresponding diagnosis;

processing circuitry configured to cause the support system to, assign a patient among the plurality of patients to a group of people based on the patient data for the patient or a diagnosis, determine a patient prevalence value relative to the diagnosis for the patient based on a group prevalence value for the group of people, the first examination result and previous examination prediction information associated with the previous examination procedure, automatically determine evaluation information corresponding to a future examination procedure among the at least one future examination procedure based on the patient prevalence value for the diagnosis and the future examination prediction information for the future examination procedure in response to determining that the patient prevalence value exceeds a threshold for the diagnosis, send the evaluation information to an imaging device to perform the future examination procedure based on the evaluation information, the evaluation information including an imaging protocol; and the imaging device including a processor configured to perform a computed tomography examination included in the future examination procedure in response to receiving the evaluation information, the performance of the computed tomography examination including implementing the imaging protocol, the performance of the computed tomography examination including directing a radiation dose to the patient.

12. A non-transitory computer readable memory storing a computer program that, when executed by processing circuitry, causes the processing circuitry to carry out the method of claim 1.

13. A non-transitory electronically readable data carrier storing that, when executed by processing circuitry, causes the processing circuitry to carry out the method of claim 1.

14. The method of claim 1, wherein the evaluation information is specific for the diagnosis.

15. The method of claim 4, wherein the negative predictive value corresponds to a user selected examination procedure.

16. The method of claim 5, wherein the at least one recommended examination procedure includes a series of recommended examination procedures.

17. The method of claim 9, further comprising:

retrieving the future examination procedure from an information system.

18. The method of claim 1, further comprising:

determining at least one of the patient prevalence value or the group prevalence value based on second patient data, the second patient data corresponding to (i) a plurality of other patients in the group of people or (ii) a plurality of other patients previously subjected to a particular examination procedure for which a ground truth for the diagnosis is derivable, and determining the previous examination prediction information corresponding to the previous examination procedure based on the second patient data.

19. The method of claim 1, wherein the automatically generating evaluation information generates the evaluation information based on, a first probability that a positive result of the future examination procedure corresponds to a correct positive diagnosis, or a second probability that a negative result of the future examination procedure corresponds to a correct negative diagnosis.

20. The method of claim 1, wherein the previous examination procedure is a computed tomography examination.

21. The method of claim 5, wherein the at least one recommended examination procedure includes a biopsy.

22. The method of claim 1, wherein the previous examination procedure comprises a calcium scoring.

23. The method of claim 1, wherein the future examination procedure includes fractional flow reserve (FFR) computed tomography.

24. The method of claim 7, wherein at least one of the performing performs the simulation, and the simulation is a Monte-Carlo simulation;

the mathematical probability model is based on a Markov chain or a Bayesian network; or the automatically generating evaluation information generates the evaluation information based on a positive predictive value or a negative predictive value.

25. The method of claim 1, wherein the automatically generating generates the evaluation information related to the future examination procedure in response to determining the future examination procedure corresponds to a greatest reliability for the diagnosis.

26. The method of claim 19, wherein the first probability is determined based on the patient prevalence value, and the automatically generating generates the evaluation information in response to determining the first probability exceeds the threshold for the diagnosis; or the second probability is determined based on the patient prevalence value, and the automatically generating generates the evaluation information in response to determining the second probability exceeds the threshold for the diagnosis.

27. The method of claim 19, wherein the automatically generating generates the evaluation information related to the future examination procedure in response to determining the first probability or the second probability is highest for the future examination procedure with respect to the diagnosis.

28. The method of claim 1, wherein the evaluation information is first evaluation information, and the future examination procedure is a first future examination procedure; and the method further comprises:

updating, by the processing circuitry, the patient prevalence value based on a result of the computed tomography examination of the first future examination procedure to obtain an updated patient prevalence value, automatically generating, by the processing circuitry, second evaluation information related to a second future examination procedure in response to determining that the updated patient prevalence value does not exceed the threshold for the diagnosis, the second future examination procedure including directing a radiation dose to the patient, and outputting, by the processing circuitry, the second evaluation information in response to the automatically generating the second evaluation information, the second evaluation information indicating that the second future examination procedure should not be performed.

* * * * *